United States Patent
Mueller et al.

(10) Patent No.: US 7,822,588 B2
(45) Date of Patent: Oct. 26, 2010

(54) SURFACE REPLACEMENT OF A FEMORAL HEAD

(75) Inventors: Heiko Mueller, Munich (DE); Robert Dick, Munich (DE); Martin Adamski, Munich (DE); Gregor Tuma, Munich (DE)

(73) Assignee: BrainLAB AG, Feldkirchen (DE)

( * ) Notice: Subject to any disclaimer, the term of this patent is extended or adjusted under 35 U.S.C. 154(b) by 736 days.

(21) Appl. No.: 11/755,024

(22) Filed: May 30, 2007

(65) Prior Publication Data
US 2008/0009954 A1 Jan. 10, 2008

Related U.S. Application Data

(60) Provisional application No. 60/806,504, filed on Jul. 3, 2006.

(30) Foreign Application Priority Data
May 31, 2006 (EP) ................... 06011218

(51) Int. Cl.
*G06G 7/48* (2006.01)
(52) U.S. Cl. ......................................... 703/6
(58) Field of Classification Search ............... 703/6
See application file for complete search history.

(56) References Cited

U.S. PATENT DOCUMENTS 6,002,859 A * 12/1999 DiGioia et al. ............... 703/11
7,039,225 B2 * 5/2006 Tanaka et al. ............... 382/128
7,388,972 B2 * 6/2008 Kitson ....................... 382/128
2003/0176860 A1 * 9/2003 Shimura ...................... 606/53
2005/0065617 A1 3/2005 Moctezuma de la Barrera et al.
2005/0281465 A1 * 12/2005 Marquart et al. ............ 382/195
2006/0058886 A1 * 3/2006 Wozencroft ............. 623/22.15
2006/0264731 A1 * 11/2006 Murphy ....................... 600/407

FOREIGN PATENT DOCUMENTS

DE 20 2005 001 128 5/2005
DE 20 2005 001 127 6/2005
EP 1 563 810 8/2005

OTHER PUBLICATIONS

Zhao et al., "Fast surface reconstruction using the level set method", 2001, IEEE Workshop on Variational and Level Set Methods, pp. 194-201.*

* cited by examiner

*Primary Examiner*—Paul L Rodriguez
*Assistant Examiner*—Russ Guill
(74) *Attorney, Agent, or Firm*—Renner, Otto, Boisselle & Sklar, LLP

(57) ABSTRACT

A method for selecting a femoral implant based on models of a femoral neck and/or a femoral head of a patient is provided. A femoral neck model and/or femoral head model is produced from three-dimensional reference point spatial positions of the femoral neck or head, and a base size of a femoral implant model is ascertained based on the femoral head model. A femoral implant model is produced from the base size, and the implant model is positioned at a position in or on the femoral head model. An implant value is ascertained that indicates how many or what proportion of the ascertained reference point spatial positions are outside the implant model. If the implant value exceeds a predetermined value, the implant model is repositioned and the process is repeated. If the implant value does not exceed the value, an appropriate size and position of the implant is determined.

24 Claims, 4 Drawing Sheets

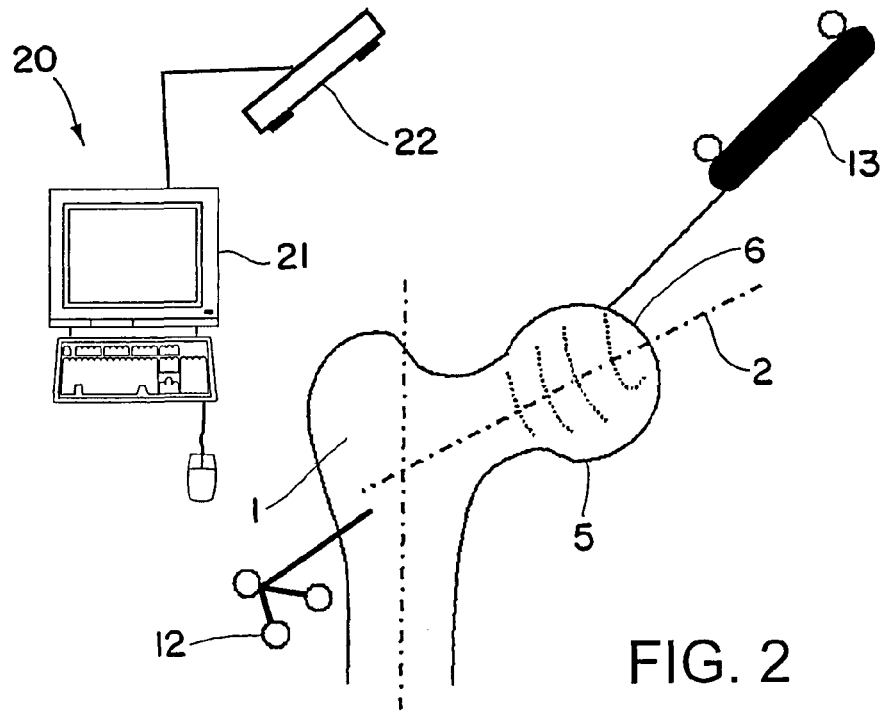
FIG. 2
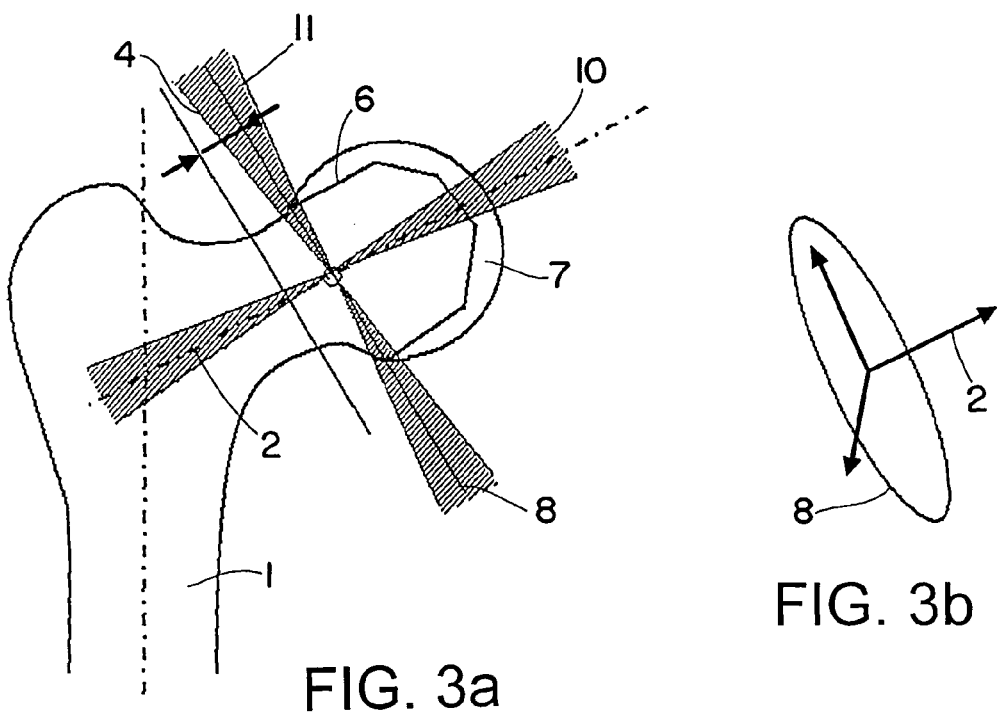
FIG. 3a
FIG. 3b

| | |
|---|---|
| 1 H | |
| 1 P | |
| 1 F | |
| 1 A | |
| 1 P | 1 H |
| 1 P | 1 F |
| 1 A | 1 H |
| 1 A | 1 F |
| 2 H | 1 A |
| 2 H | 1 P |
| 2 P | 1 F |
| 2 P | 1 H |
| 1 A | 2 F |
| 1 P | 2 F |
| 2 A | 1 F |
| 2 P | 1 H |
| 2 A | 2 F |
| 2 P | 2 F |
| 2 A | 2 H |
| 2 P | 2 H |

FIG. 4

SURFACE REPLACEMENT OF A FEMORAL HEAD

RELATED APPLICATION DATA

This application claims priority of U.S. Provisional Application No. 60/806,504 filed on Jul. 3, 2006, which is incorporated herein by reference in its entirety.

FIELD OF THE INVENTION

The present invention relates generally to femoral implants and, more particularly, to a method and device for selecting a femoral implant for attachment to a femoral head during hip joint operations, wherein the femoral implant is selected based on virtual or digital models of a femoral neck and/or a femoral head of a patient.

BACKGROUND OF THE INVENTION

In hip joint operations the femoral neck is usually retained and the femoral head is fraised off. This enables a surface of a replacement femoral head or a femoral implant to be cemented onto or into the fraised femoral head. If a femoral implant is selected that is too small (e.g., an inner diameter of the implant is too small) and cemented on the fraised head, there exists the danger that the fraiser apparatus that processes the inner contour of the implant is unintentionally fraised into the femoral neck so as to cause a fracture of the femoral neck. If a femoral implant is selected that is too large, then the femoral implant may not be sufficiently flush with the femoral head or on the femoral neck.

In conventional methods, the implant size is pre-operatively determined using x-rays and templates. This procedure can be time-consuming and can include a number of possible inaccuracies due to projection errors. Further, the determined size may be intra-operatively verified by means of measuring templates or metal templates, which increases the amount of time expended in implementing the procedure.

SUMMARY OF THE INVENTION

A femoral implant or a femoral head replacement or attachment is ascertained from models of a femoral neck and/or a femoral head of a patient. Reference points, such as anatomical landmarks, can be detected on the femoral neck or femoral head of the patient. These reference points may be detected using a contact or contactless process. For example, a laser pointer may be used to contactlessly scan a surface of the femur so as to create points thereon, or a mechanical pointer can be used to physically touch points on the femur. These points (e.g., the reflections on the surface or the physical location of the pointer tip) then can be provided to a navigation system. Further, a trackable object (e.g., a reference star that emits or reflects infrared radiation) may be arranged on the femoral neck. The reference star, via the radiation emitted therefrom, can be detected by a camera, such as an infrared camera, of the navigation system. From this information, the navigation system can ascertain the three-dimensional spatial position of the reference star relative to a reference coordinate system. Further, from the detected reference points of the femoral neck and/or femoral head, the navigation system can ascertain three-dimensional reference point spatial positions of the detected reference points relative to the reference coordinate system (e.g., the reference star or the origin of the reference star) based on the ascertained three-dimensional spatial positions of the reference star. Then, the femoral neck and/or femoral head can be registered with respect to the reference coordinate system.

A model of the femoral neck and/or femoral head, such as a virtual or digital model of the femoral neck and/or femoral head, can be ascertained from the ascertained three-dimensional reference point spatial positions. The models can be ascertained, for example, by connecting the ascertained reference point spatial positions to form a continuous shape or surface. Alternatively, the models may be ascertained by approximating a shape or surface of the femoral neck and/or femoral head from the ascertained reference point spatial positions. The model of the proximal femur comprising the femoral head and neck can be ascertained by connecting the ascertained reference point spatial coordinates to form a shape that has a spherical shape. A base or initial size of a model of the femoral implant can be ascertained from the ascertained model of the femoral head.

The size of the femoral implant model, for example, can be deduced from the size of the femoral head or from the diameter of the femoral head model. The diameter of the femoral head model can be used as a base size or base value of the inner diameter of the femoral implant model. A model of the femoral implant can be determined based on the ascertained base value of the inner diameter of the femoral implant model.

Preferably, the initial femoral implant model is not produced using the base size or the ascertained base value. Instead, a starting size or starting value of the inner diameter of the of the femoral implant model is preferably used that deviates from the base value or base size by a predetermined value and in particular is smaller than the base value or base size by a predetermined value. A size that is one, two or more size units smaller than the base size of the femoral implant model as ascertained from the size of the femoral head, for example, can be chosen as the starting size of the femoral implant model. A value that is one, two or more units smaller than the base value of the inner diameter of the femoral implant model as ascertained from the inner diameter of the femoral head (and preferably corresponding to the inner diameter of the femoral head) also can be used as the starting value of the inner diameter of the femoral implant model.

The ascertained virtual or digital femoral implant model can be placed or positioned in the virtual or digital femoral head model or virtually cemented on the head. In the cemented position, the navigation system can ascertain whether an appropriate size of the implant has been chosen using the starting value. To this end, an absolute implant value can be ascertained that indicates how many of the ascertained reference point spatial positions or of the points of the femoral head model are within or outside the femoral implant model. A value that indicates how many of the ascertained reference point spatial positions or of the points of the femoral head model are within or outside the inner diameter of the femoral implant model also can be ascertained as an absolute implant value. A relative implant value also can be ascertained that indicates what proportion of the ascertained reference point spatial positions or of the points of the femoral head model are within or outside the femoral implant model, or that indicates what proportion of the ascertained reference point spatial positions or points of the femoral head model are within or outside the inner diameter of the femoral implant model. Preferably, an absolute implant value is ascertained that indicates how many of the reference point spatial positions are outside the inner diameter of the femoral implant model, or a relative implant value that indicates what proportion of the ascertained reference point spatial positions are outside the inner diameter of the femoral implant model.

The ascertained implant value can be compared with a predetermined limit value or a limit value derived, for example, from the base value of the femoral implant. If an implant value indicative of how many or what proportion of the ascertained reference point spatial positions are outside the inner diameter of the femoral implant model exceeds the limit value, then it may be deduced that the chosen femoral implant model is too small for the femoral head in question or is arranged in an incorrect position. In this case, the femoral implant model can be virtually moved, for example by shifting, to another predetermined or ascertainable position. In this new position of the femoral implant model, an implant value can again be ascertained, which may be compared with the predetermined limit value, wherein it is again possible to deduce from the comparison with the limit value whether an appropriate size and position of the femoral implant has been found or whether the femoral implant is to be repositioned again and checked again for appropriate size and shape. If the implant value falls below the limit value, it may be deduced that the femoral implant model exhibits a correct size and is correctly positioned, such that by taking these data into account, a surgeon, for example, can position a femoral implant having the ascertained size at the ascertained position.

If the implant value does not fall below the limit value in any of the positions, or exceeds it in every position, then a new femoral implant model having a larger size or inner diameter than the previous size or inner diameter is preferably calculated. The inner diameter of the femoral implant model, for example, can be increased by one, two or more units. The larger femoral implant model is preferably positioned again and checked for size and position at different positions by means of the implant value.

Ascertaining an appropriate femoral implant model can be performed until an appropriate or the first appropriate femoral implant is found, or all the appropriate sizes and positions of the femoral implant that conform to the predetermined limit values can be ascertained. An ideal femoral implant can be selected from all the appropriate models and proposed by the navigation system and/or can be chosen by a surgeon.

Preferably, a model of the femoral neck axis of the femoral neck also is determined from the ascertained reference point spatial positions. In particular, the femoral neck axis model is determined from the reference point spatial positions ascertained on the femoral neck, wherein the femoral neck axis model is preferably calculated as an intersecting straight line of at least two planes. The planes, for example, can be planes running anteriorly, posteriorly, inferiorly or superiorly through the body of the patient.

From the reference point spatial positions, in particular the reference point spatial positions at the interface between the femoral neck and the femoral head, a model of a plane through the connection between the femoral neck and the femoral head can be ascertained in the femoral neck model and the femoral head model. The connection between the femoral neck and the femoral head can span or form a three-dimensional coordinate system with the femoral neck axis, wherein said three-dimensional coordinate system can be used as a coordinate system with respect to which calculations, such as the implant value calculations, of the navigation system can be performed.

The femoral implant model can be shifted in order to reposition the femoral implant model for ascertaining a suitable position or an appropriate position of the femoral implant. Preferably, the femoral implant model is shifted such that a center axis or the femoral neck axis through the implant and the femoral head is not translationally shifted or does not perform a translational movement. Preferably, the femoral implant model is shifted in a direction, in particular anteriorly, superiorly, posteriorly or inferiorly, that is perpendicular to the model of the femoral neck axis, such that it is translationally moved perpendicular to the center axis or femoral neck axis, but not along the center axis or femoral neck axis. The femoral implant model can thus be repositioned by changing the position of the femoral neck axis model in the femoral neck model and/or femoral head.

The methods for creating the models described herein may be implemented by a computer system, for example. In this sense, the method can be embodied as a computer program which, when it is loaded onto a computer or is running on a computer, performs a method as described above. The computer program also may be embodied on a computer readable medium.

A device for assisting in performing a femoral implant or a femoral head replacement/attachment includes: a navigation system having at least one camera, preferably an infrared camera; a detection unit that can be connected via a wired or wireless link to the navigation system or can be integrated into the navigation system; and a computational unit that can be connected via a wired or wireless link the navigation system or can be integrated into the navigation system. Reference points on a femoral neck and/or femoral head of a patient can be detected by the detection unit, such as reference points created by a pointer or laser pointer and detected by a camera. Preferably, anatomical landmarks of the femoral neck and/or femoral head are detected. The position of a reference star arranged on the femoral neck, preferably a reference star that emits or reflects infrared radiation, can be spatially detected and tracked by the camera of the navigation system.

From the ascertained reference points, and taking into account the ascertained positions of the reference star, the computational unit can ascertain three-dimensional reference point spatial positions of the detected reference points. From the ascertained positions, the femoral neck and/or femoral head can be registered. The computational unit can produce a model of the femoral neck and/or femoral head, such as a spherical femoral head from the registered data or the three-dimensional reference point spatial positions. Alternatively, the computational unit can produce an approximated virtual or digital model of the femoral neck and/or femoral head. Based on the produced femoral head model, the computational unit can determine a base size of a femoral implant model. The computational unit, for example, can calculate the diameter of the femoral head from the reference point spatial positions and use this diameter to ascertain the base size of the femoral implant model. The ascertained diameter of the femoral head is preferably used as the base value of the inner diameter of the femoral implant model. The computational unit can produce a femoral implant model based on the ascertained basic size of the femoral implant.

A starting size that deviates from the base size and is preferably one, two or more units smaller than the base size of the femoral implant model can be used as a starting value or starting size of the femoral implant model. An inner diameter deviating from the ascertained base value of the inner diameter can be used as the starting value of the inner diameter of the femoral implant model. Preferably, an inner diameter that is one, two or more units smaller is used by the computational unit as the starting value of the inner diameter of the femoral implant model.

The femoral implant model produced using the starting values or the starting size can be virtually placed or positioned in or on the femoral head model by the computational unit.

This virtual positioning also can be graphically displayed on a display device. The ascertained reference point spatial positions or points of the femoral head model also may be compared with the femoral implant model by the computational unit. The computational unit then ascertains whether the femoral implant model is large enough for the femoral head model. Preferably, the computational unit ascertains an implant value that indicates how many or what proportion of the ascertained reference point spatial positions or points of the femoral head model are outside the femoral implant model or outside the inner diameter of the femoral implant. If the ascertained implant value is above a predetermined limit value, then the femoral implant model may be repositioned and a new implant value may be ascertained or a larger femoral implant model may be ascertained. Preferably, the implant value of this model is determined at different positions. The computational unit preferably determines an appropriate or possible size and position of the femoral implant when the implant value does not exceed the limit value. Preferably, the appropriate femoral implant or implants is/are output or displayed by the computational unit on a display device, such that a surgeon can select the ideal femoral implant.

BRIEF DESCRIPTION OF THE DRAWINGS

The forgoing and other features of the invention are hereinafter discussed with reference to the drawing.

FIG. 2 illustrates reference points of a femoral head being ascertained in accordance with the invention.

FIG. 3A is an exemplary virtual model of the femoral neck, the femoral head and the femoral implant in accordance with the invention FIG. 3B is an exemplary virtual coordinate system of the arrangement from FIG. 3A.

FIG. 4 is a chart illustrating an exemplary progression of shifts of a femoral implant in accordance with the invention.

DETAILED DESCRIPTION

Figure 1:
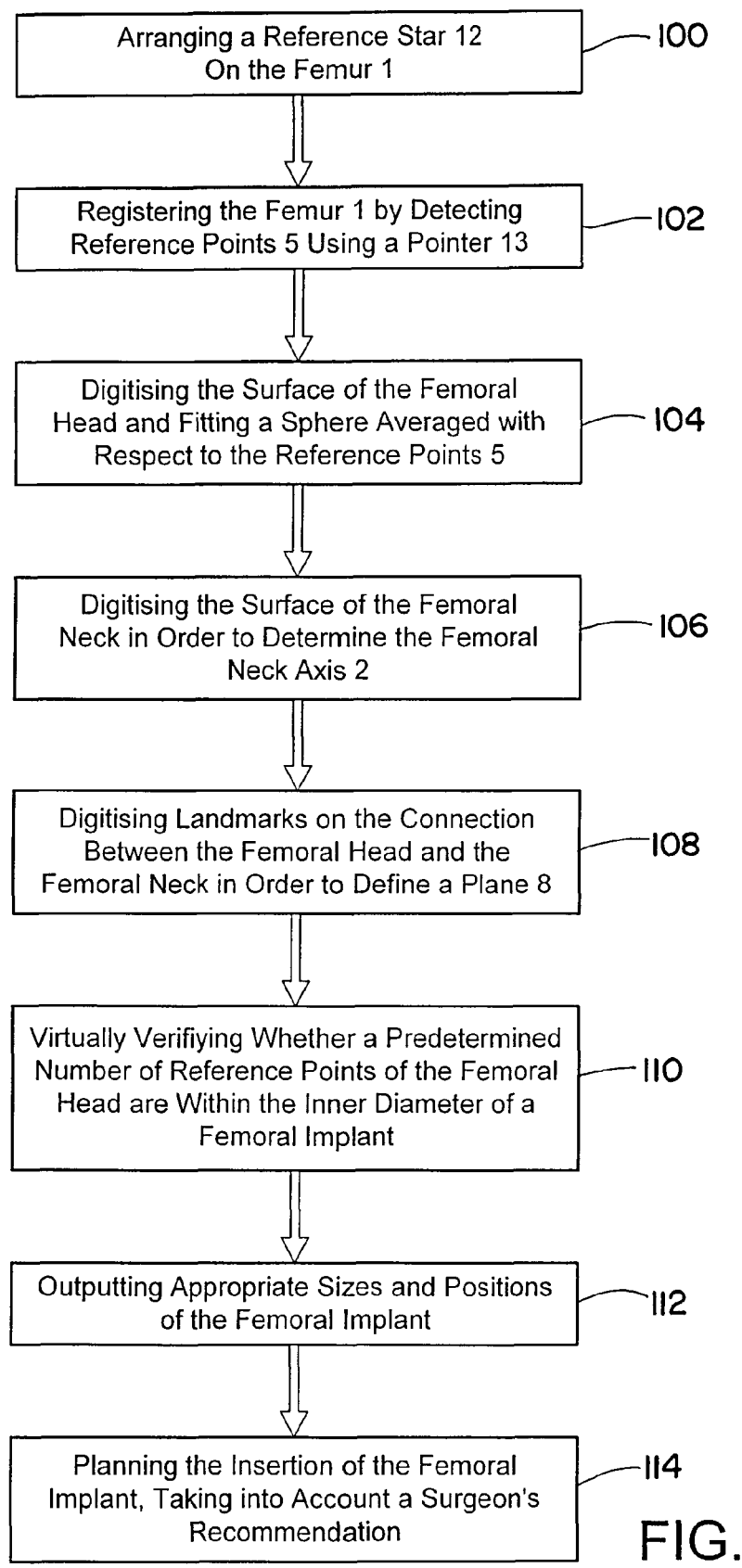
FIG. 1 is a flow diagram of an exemplary method for ascertaining or selecting a femoral implant or a femoral head replacement from models of a femoral neck and/or a femoral head of a patient in accordance with the invention.

FIG. 1 shows a flow diagram of an exemplary method for ascertaining or selecting a femoral implant or a femoral head replacement or attachment from models of a femoral neck and/or a femoral head. With additional reference to FIG. 2, a reference star 12 that reflects or emits infrared radiation is arranged on the femur 1, as indicated at block 100. A position of the reference star 12 can be ascertained by an infrared camera 22 of a navigation system 20. By means of a pointer 13, the surface of a fraised-off femoral head 6 is scanned and reference points 5 of the femoral head 6 are detected by the camera 22 and provided to the navigation system 20, as indicated at block 102. The spatial position of the reference points can be ascertained by the navigation system 20 and, thus, the femur 1 can be registered.

By means of the ascertained reference points 5, the surface of the femoral head 6 also can be digitized by forming a virtual model of the femoral head 6, as indicated at block 104. A shape or surface of the femoral head 6 can be approximated to the ascertained reference points 5. The approximated shape, such as a spherical shape, may be fit between the ascertained reference points 5 such that the mean error or mean distance between the reference points 5 and the surface of the sphere is minimal. The surface of the femur 1 may be digitized on the basis of the detected and ascertained reference points 5 on the femur 1. At block 106, the femoral neck axis 2 of the model can be ascertained from the digitized model of the femur 1.

At block 108, and with further reference to FIG. 3A, a connection plane 8 that runs through the connection between the femoral head 6 and the femoral neck 1 can be ascertained from the detected points or landmarks on the connection between the femoral head 6 and the femoral neck 1. Two spatial directions are defined by the plane 8, such that a three-dimensional coordinate system (e.g., as can be seen in FIG. 3B) may be ascertained from the plane 8 and the femoral neck axis 2. Calculations made by the navigation system 20 may be performed with respect to the coordinate system defined by the connection plane 8 and the femoral neck axis 2.

On the basis of the data provided, such as the reference points 5 of the femoral head 6 and the model of the femoral implant 7, the navigation system 20 can calculate whether a predetermined number of reference points 5 of the femoral head 6 are within the inner diameter of the femoral implant 7, as indicated at block 110. If more reference points 5 of the femoral head 6 are within the femoral implant 7 than a predetermined threshold value, then the femoral implant 7 has a sufficient size, such that the selected size and the selected position of the femoral implant 7 are classified as being appropriate and the data of the femoral implant 7 are outputted at block 112.

If fewer reference points 5 of the femoral head 6 are within the inner diameter of the femoral implant 7 than the predetermined threshold value, then the navigation system 20 assumes that the selected femoral implant 7 is too small and/or has been incorrectly positioned. In this case, the femoral implant 7 can be anteriorly, superiorly, posteriorly or inferiorly shifted, such that the center axis or femoral neck axis 2 is not translationally shifted, but rather (as shown in FIG. 3A) its spatial position is changed or rotated, wherein the plane 8 is also rotated. In this new position of the femoral implant 7, it is again ascertained whether the implant value exceeds or falls below the predetermined threshold value. If more reference points 5 of the femoral head 6 are outside the inner diameter of the femoral implant 7, this position of the femoral implant 7 is assumed to not be a possible or appropriate position for positioning the femoral implant under examination. If all the possible positions of the femoral implant 7 have been examined, then the size or inner diameter of the femoral implant 7 is increased and a check is again made in the possible positions as to whether the implant value exceeds or falls below the threshold value of the larger model of the femoral implant.

All the sizes and shapes for which it is ascertained that a sufficient number of reference points 5 of the femoral head 6 are within the inner diameter of the femoral implant 7 are assumed to be appropriate sizes and shapes and positions of the femoral implant 7 and are output. At block 114, the surgeon can select the ideal femoral implant 7 from these output sizes and positions of the femoral implant 7.

Moving to FIG. 4, an exemplary progression of possible shifts or repositioning of a femoral implant 7 of a particular size are shown. The model of the femoral implant 7 of one size can be shifted to all the positions shown in FIG. 4, where it is tested for exceeding the threshold value. The letter "H" indicates a shift in the direction of the head, the letter "F" indicates a shift in the direction of the feet, the letter "A" indicates a shift anteriorly and the latter "P" indicates a shift posteriorly, each proceeding from the previous position of the femoral implant model 7. The numerical values indicate how far or by how many units the femoral implant 7 is shifted in the respectively chosen direction.

Figure 5:
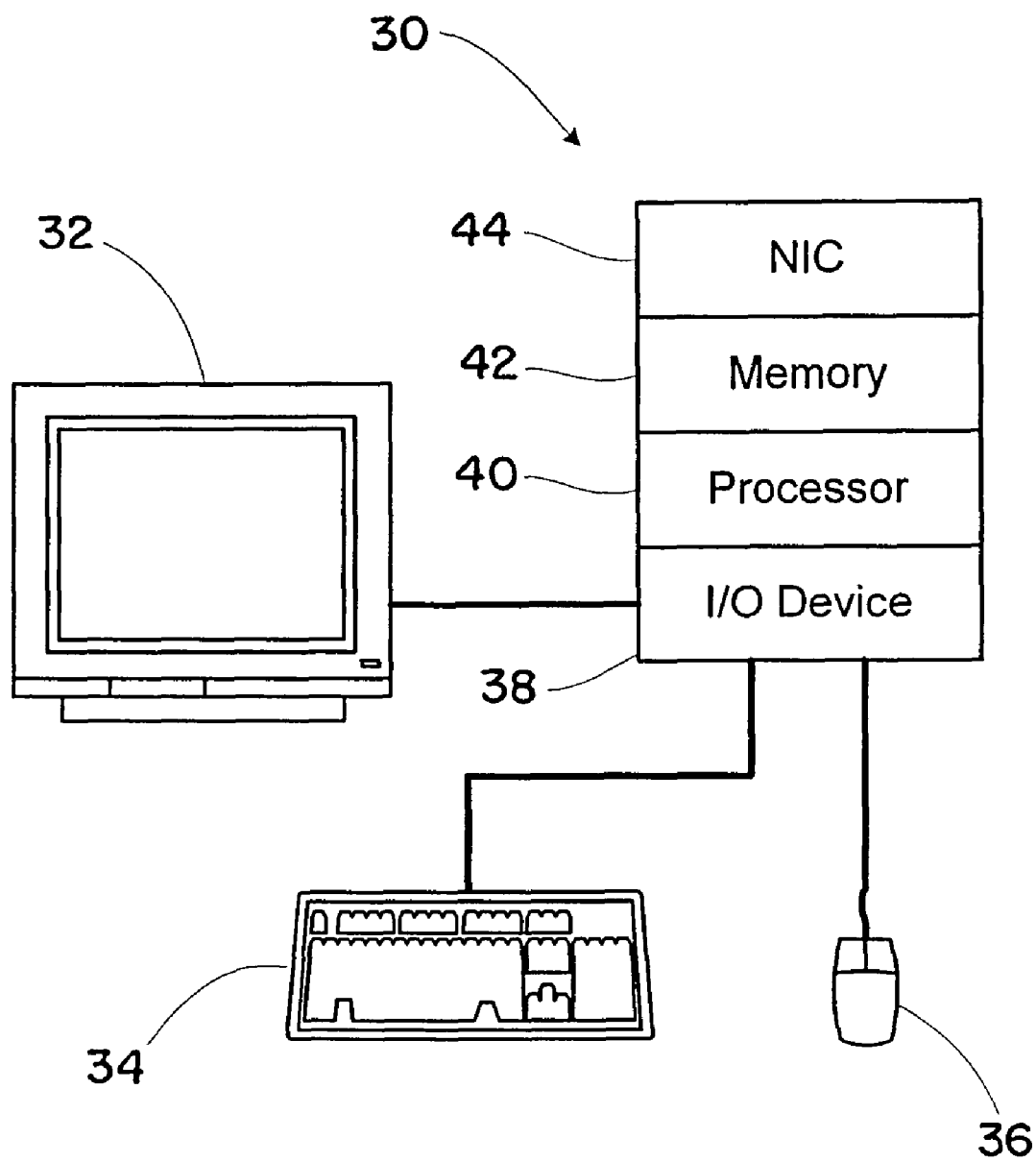
FIG. 5 is a block diagram of an exemplary computer system that can be used to carry out the method in accordance with invention.

Moving now to FIG. 5 there is shown a block diagram of a computer system 30 that may be used to implement one or more of the methods described herein. The computer system may be a stand alone system, or it may be part of the navigation system 20 described herein. The computer system 30 may include a display 32 for viewing system information, and a keyboard 34 and pointing device 36 for data entry, screen navigation, etc. A computer mouse or other device that points to or otherwise identifies a location, action, etc., e.g., by a point and click method or some other method, are examples of a pointing device 36. Alternatively, a touch screen (not shown) may be used in place of the keyboard 34 and pointing device 36. The display 32, keyboard 34 and mouse 36 communicate with a processor via an input/output device 38, such as a video card and/or serial port (e.g., a USB port or the like).

A processor 40, such as an AMD Athlon 64® processor or an Intel Pentium IV® processor, combined with a memory 42 execute programs to perform various functions, such as data entry, numerical calculations, screen display, system setup, etc. The memory 42 may comprise several devices, including volatile and non-volatile memory components. Accordingly, the memory 42 may include, for example, random access memory (RAM), read-only memory (ROM), hard disks, floppy disks, optical disks (e.g., CDs and DVDs), tapes, flash devices and/or other memory components, plus associated drives, players and/or readers for the memory devices. The processor 40 and the memory 42 are coupled using a local interface (not shown). The local interface may be, for example, a data bus with accompanying control bus, a network, or other subsystem.

The memory may form part of a storage medium for storing information, such as application data, screen information, programs, etc., part of which may be in the form of a database. The storage medium may be a hard drive, for example, or any other storage means that can retain data, including other magnetic and/or optical storage devices. A network interface card (NIC) 44 allows the computer system 30 to communicate with other devices.

A person having ordinary skill in the art of computer programming and applications of programming for computer systems would be able in view of the description provided herein to program a computer system 30 to operate and to carry out the functions described herein. Accordingly, details as to the specific programming code have been omitted for the sake of brevity. Also, while software in the memory 42 or in some other memory of the computer and/or server may be used to allow the system to carry out the functions and features described herein in accordance with the preferred embodiment of the invention, such functions and features also could be carried out via dedicated hardware, firmware, software, or combinations thereof, without departing from the scope of the invention.

Computer program elements of the invention may be embodied in hardware and/or in software (including firmware, resident software, micro-code, etc.). The invention may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium such as the Internet. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for selecting a femoral implant based on models of a femoral neck and/or a femoral head of a patient, comprising:
   a) detecting reference points on the femoral neck and/or femoral head of the patient;
   b) registering the femoral neck and/or femoral head based on three-dimensional reference point spatial positions of the detected reference points;
   c) producing a femoral neck model and/or femoral head model from the three-dimensional reference point spatial positions;
   d) ascertaining a base size of a femoral implant model based on the femoral head model;
   e) producing the femoral implant model based on the base size of the femoral implant model;
   f) positioning the femoral implant model at a position in or on the femoral head model;
   g) ascertaining, using a processor, an implant value that indicates how many or what proportion of the ascertained reference point spatial positions are outside the femoral implant model;
   h) determining if the implant value exceeds a predetermined limit value; and
   i) if the implant value exceeds the limit value, repositioning the femoral implant model and performing steps g) to i), or if the implant value does not exceed the limit value, determining an appropriate size and position of the femoral implant.

2. The method according to claim 1, wherein detecting reference points includes detecting anatomical landmarks as the reference points.

3. The method according to claim 1, further comprising repeating steps f) to i) using at least one other femoral implant model that is different from the femoral implant model based on the base size.

4. The method according to claim 3, where using at least one other femoral implant model includes using a model that is larger in size than the femoral implant model produced in step e).

5. The method according to claim 3, wherein using at least one other femoral implant model includes using a femoral implant model that exhibits a larger inner diameter than the femoral implant model produced in step e).

6. The method according to claim 1, wherein ascertaining the base size of the femoral implant model includes using a diameter of the produced femoral head model as a base value of an inner diameter of the femoral implant, and using the inner diameter of the femoral implant as the base size of the femoral implant model.

7. The method according to claim 6, wherein producing the femoral implant model includes using as a starting value the inner diameter of the femoral implant model, wherein the starting value deviates from the base value of the inner diameter of the femoral implant by a predetermined value.

8. The method according to claim 7, wherein the starting value of the inner diameter of the femoral implant model is smaller than the base value by a predetermined value.

9. The method according claim 1, further comprising selecting the femoral implant based on the number or proportion of the ascertained reference point spatial positions that are outside an inner diameter of the femoral implant model.

10. The method according to claim 1, wherein producing the femoral head model from the three-dimensional reference point spatial positions includes ascertaining a shape or surface from the reference point spatial positions to form the femoral head model.

11. The method according to claim 1, further comprising ascertaining a femoral neck axis model from the reference point spatial positions.

12. The method according to claim 11, wherein ascertaining the femoral neck axis model includes ascertaining the neck axis model as an intersecting straight line of at least two planes, wherein the planes run anteriorly, superiorly, posteriorly and inferiorly through the patient.

13. The method according to claim 12, further comprising ascertaining from the reference point spatial positions a plane through a line connecting the femoral neck and the femoral head in the models of the femoral neck and the femoral head.

14. The method according to claim 13, wherein ascertaining from the reference point spatial positions the plane through the line connecting the femoral neck and the femoral head in the models of the femoral neck and the femoral head includes using the reference point spatial positions of a connection between the femoral neck and the femoral head.

15. The method according to claim 11, wherein repositioning the femoral implant model includes shifting the femoral implant model in a direction that is perpendicular to the femoral neck axis model.

16. The method according to claim 15, wherein shifting the femoral implant model in a direction that is perpendicular to the femoral neck axis model includes anteriorly, superiorly, posteriorly or inferiorly shifting the femoral implant model in a direction that is perpendicular to the femoral neck axis model.

17. The method according to claim 11, wherein repositioning the femoral implant model includes changing the position of the femoral neck axis model relative to the femoral implant model in the femoral neck model.

18. The method according to claim 1, wherein repositioning the femoral implant model includes shifting the femoral implant model in all degrees of freedom relative to the femoral head model.

19. The method according to claim 1, further comprising ascertaining and outputting a number of appropriate shapes and sizes of the femoral implant.

20. The method according to claim 1, further comprising ascertaining and outputting a size and shape of the femoral implant.

21. A computer program embodied on a computer readable storage medium for selecting a femoral implant based on models of a femoral neck and/or a femoral head of a patient, comprising:
   a) code that detects reference points on the femoral neck and/or femoral head of the patient;
   b) code that registers the femoral neck and/or femoral head based on three-dimensional reference point spatial positions of the detected reference points;
   c) code that produces a femoral neck model and/or femoral head model from the three-dimensional reference point spatial positions;
   d) code that ascertains a base size of a femoral implant model based on the femoral head model;
   e) code that produces a femoral implant model based on the base size of the femoral implant model;
   f) code that positions the femoral implant model at a position in or on the femoral head model;
   g) code that ascertains an implant value that indicates how many or what proportion of the ascertained reference point spatial positions are outside the femoral implant model;
   h) code that determines if the implant value exceeds a predetermined limit value; and
   i) code that repositions the femoral implant model and performing steps g) to i) if the implant value exceeds the limit value, or determines an appropriate size and position of the femoral implant if the implant value does not exceed the limit value.

22. A device for selecting a femoral implant based on models of a femoral neck and/or a femoral head of a patient, comprising:
   a detection unit for detecting reference points on the femoral neck and/or femoral head of the patient;
   a navigation system operatively connected to the detection unit and comprising at least one camera for detecting the position of a reference star arranged on the femoral neck; and
   a computational unit operatively connected to the navigation system and operative to:
      a) register the femoral neck and/or femoral head based on three-dimensional reference point spatial positions of the detected reference points;
      b) produce a femoral neck model and/or femoral head model from the three- dimensional reference point spatial positions;
      c) ascertain a base size of a femoral implant model based on the produced femoral head model;
      d) produce a femoral implant model based on the base size of the femoral implant model;

e) ascertain an implant value that indicates how many or what proportion of the ascertained reference point spatial positions are outside the femoral implant model;
f) determine if the implant value exceeds a predetermined limit value; and
g) determine an appropriate size and position of the femoral implant if the implant value does not exceed the limit value.

23. The device according to claim 22, wherein the camera is an infrared camera.

24. The device according to claim 22, further comprising an output device operatively connected to the navigation system, said output device operative to graphically display the femoral neck model, the femoral head model and the femoral implant model.

* * * * *